United States Patent [19]
Adam et al.

[11] Patent Number: 5,701,898
[45] Date of Patent: Dec. 30, 1997

[54] METHOD AND SYSTEM FOR DOPPLER ULTRASOUND MEASUREMENT OF BLOOD FLOW

[75] Inventors: Dan R. Adam, Haifa, Israel; Kenneth M. Kempner; Mark A. Vivino, both of Bethesda, Md.; Eben E. Tucker, Silver Spring, Md.; Michael Jones, Bethesda, Md.

[73] Assignee: The United States of America as represented by the Department of Health and Human Services, Washington, D.C.

[21] Appl. No.: 651,022

[22] Filed: May 21, 1996

Related U.S. Application Data

[63] Continuation of Ser. No. 300,718, Sep. 2, 1994, abandoned.
[51] Int. Cl.$^6$ .................................................. A61B 8/06
[52] U.S. Cl. ........................... 128/661.09; 128/661.1
[58] Field of Search .................... 128/660.04, 660.05, 128/660.07–660.1; 364/413.25

[56] References Cited

U.S. PATENT DOCUMENTS

| | | | |
|---|---|---|---|
| 4,103,679 | 8/1978 | Aronson | 128/661.1 |
| 4,501,279 | 2/1985 | Seo | 128/661.1 |
| 4,787,395 | 11/1988 | Yanashima et al. | |
| 4,791,567 | 12/1988 | Cline et al. | |
| 4,821,731 | 4/1989 | Martinelli et al. | 128/662.06 |
| 4,980,865 | 12/1990 | Ishibashi et al. | |
| 4,984,160 | 1/1991 | Saint Felix et al. | |
| 4,991,224 | 2/1991 | Takahashi et al. | |
| 4,991,589 | 2/1991 | Hongo et al. | |
| 5,078,145 | 1/1992 | Furubata | 128/916 X |
| 5,090,411 | 2/1992 | Higuchi | |
| 5,105,816 | 4/1992 | Shimura et al. | |
| 5,107,841 | 4/1992 | Sturgill | |
| 5,174,294 | 12/1992 | Saito et al. | |
| 5,215,093 | 6/1993 | Miyazaki et al. | |
| 5,235,857 | 8/1993 | Anderson | |
| 5,280,787 | 1/1994 | Wilson et al. | 128/661.1 |
| 5,282,471 | 2/1994 | Sato | 128/661.09 |
| 5,295,486 | 3/1994 | Wollschläger et al. | 128/916 X |
| 5,353,354 | 10/1994 | Keller et al. | 382/6 |
| 5,390,677 | 2/1995 | Ferrera et al. | 128/661.09 |
| 5,398,691 | 3/1995 | Martin et al. | 128/662.06 |
| 5,505,204 | 4/1996 | Picot et al. | 128/661.1 |

OTHER PUBLICATIONS

Moritz WE, Pearlman AS, McCabe DH, Medema DK, Ainsworth ME, Boles MS: An Ultrasound Technique For Imaging The Ventricle In Three–Dimensions and Calculating Its Volume. IEEE Trans. Biomed Eng. 1983; 30:482–492.

Geiser EA, Ariet M, Conetta DA, Lupkiewicz SM, Christie LG, Conti CR: Dynamic Three–Dimensional Echocardiographic Reconstruction of the Intact Human Left Ventricle: Technique and Initial Observations In Patients. AM Heart J 1982; 103: 1056–1065.

(List continued on next page.)

*Primary Examiner*—Francis Jaworski
*Attorney, Agent, or Firm*—Morgan & Finnegan, LLP

[57] ABSTRACT

A method and system for providing Doppler data that is corrected for misalignment between the flow direction within a vessel and the beam orientation of the ultrasound probe. A conventional ultrasonic Doppler color mapping system is adapted to include a system to measure and record the free space position and orientation of the ultrasonic probe, as well as a system to generate and record the experiment time. A set of 2D image planes is acquired, each plane labelled with time, position, and orientation data. A structural representation according to the acquired data is used to determine the flow direction for the imaged vessel structure. Based on this identified flow direction, and the orientation and position information for each acquired 2D slice, the 2D Doppler signals are appropriately transformed into corrected velocity values. These corrected velocity values may then be used to construct a 3D flow field as a function of time.

20 Claims, 3 Drawing Sheets

OTHER PUBLICATIONS

Sawada H. Fujii J, Kato K, Onoe M., Kuno K: Three–Dimensional Reconstruction of the Left Ventricle From Multiple Cross Sectional Echocardiograms; Value For Measuring Left Ventricle Volume. Br Heart J 1983; 50:438–442.

McCann HA, Chandrasekaran K, Hoffman EA, Sinak LJ, Kinter TM, Greenleaf JF: A Method For Three–Dimensional Ultrasonic Imaging of the Heart In Vivo. Dynamic Cardiovasc Imaging 1987; 1:97–109.

Levine RA, Handschumacher MD, Sanfilippo AJ, Hagege AA, Harrigan P, Marshall JE, Weyman AE: Three–Dimensional Echocardiographic Reconstruction of the Mitral Valve, With Implication For The Diagnosis of Mitral Valve Prolapse. Circulation, 1989; 80: 589–598.

Martin RW, Bashein G: Measurement of stroke Volume with three–dimensional Transeophageal Ultrasonic Scanning: Comparison With Thermodilution Measurement. Anesthesiology 1989; 70:470–476.

Martin RW, Bashein G, Detmer PR, Moritz WE: Ventricular Volume Measurement From a Multiplanar Transesophageal Ultrasonic Imaging System: An In Vitro Study. IEEE Trans Biomed Eng. 1990; 37:442–449.

Kuroda T, Kinter TM, Seward JB, Yanagi H, Greenleaf JF: Accuracy of Three–Dimensional Volume Measurement Using Biplane Transesophagael Echocardiographic Probe: In Vitrp Experiment. J. Am Soc Echocardiogr 1991; 4:475–484.

Martin RW, Bashein G, Nessly ML, Sheehan FH: Methodology for Three–Dimensional Reconstruction of the Left Ventricle From Transesophageal Echocardiograms. Ultrasound in Med & Biol 1993; 19(1): 27–38.

Picot PA, Rickey DW, Mitchell R, Rankin RN, Fenster A: Three–Dimensional Colour Doppler Imaging. Ultrasound in Medicine and Biolog, vol. 19, No. 2, 1963, Official Journal of the World Federation for Ultrasound in Medicine and Biology; pp. 95–104.

Kitney RI, Moura L, Straughan K: 3–D Visualization Of Arterial Structures Using Ultrasound and Voxel Modeling. Int J Card Imaging 1989; 4:135–143.

Potkin BN, Bartorelli AL, Gessert JM, Neville RF, Almagor Y, Roberts WC, Leon MB: Coronary Artery Imaging With Intravascular High–Frequency Ultrasound. Circulation 1990; 81: 155–1585.

Nissen SE, Grines CL, Gurley JC, Sublett K, Haynie D, Diaz C, Booth DC, DeMaria AN: Application Of A New Phased–Array Ultrasound Imaging Catheter in the Assessment of Vascular Dimensions. Circulation 1990; 81:660–666.

Rosenfield K, Losordo DW, Ramaswamy K, Pastore JO, Langevin RE, Razvi S, Kosowsk BD, Isner JM: Three–Dimensional Reconstruction of Human Coronary and Peripheral Arteries From Images Recording During Two–Dimensional Intravascular Ultrasound Examination. Circulation 1991; 84:1938–1956.

METHOD AND SYSTEM FOR DOPPLER ULTRASOUND MEASUREMENT OF BLOOD FLOW

This is a continuation of application Ser. No. 08/300,718, filed on Sep. 2, 1994 and now abandoned.

TECHNICAL FIELD

The present invention relates generally to ultrasound imaging and, more particularly, to a method and system for three dimensional (3D) color Doppler ultrasound imaging of measured blood flow.

BACKGROUND OF THE INVENTION

In the past, various methods have been applied to the problem of reconstructing 3D anatomical structures within the cardiovascular system, from 2D ultrasound images (e.g. the contour of the entire heart, or of the left ventricle). Multiple images of structural cross-sections of the heart have been taken at various orientations in order to reconstruct its shape. Since the introduction of esophageal probes, the better image quality and the nearly fixed location of the ultrasound transducer within the body have made these systems well suited for 3D reconstruction. The accuracy for volume measurements has also been demonstrated. In addition, the further development of miniaturized probes has allowed intravascular generation of 2D images and therefore, the 3D reconstruction and visualization of arterial structures, including coronary arteries. In all these cases, the accuracy and the sources of error could be studied by the use of an anatomical phantom.

These methods are slowly being adapted for flow measurements. There is clearly a clinical demand for measurement of the flow velocity pattern across the flow field. In the study and development of artificial cardiac valves, quantitative assessment of the 3D flow jets through and around have valve is required. Blood volume and its velocity in the artery have significant effects on transport of metabolic constituents and exchange of substances from blood to the endothelial cells. Also, the velocity distribution across the artery is assumed to be one of the determinants of endothelial layer damage and arterial stenosis. The large shear stresses associated with high velocities cause shear-induced platelet aggregation.

Different modalities have been tested for the determination of 3D flow velocity patterns—Ultrasound, fast Computed Tomography, and Magnetic Resonance Imaging (MRI). Various approaches have been taken to allow flow velocity mapping. Validations of the MRI measurements versus flow phantoms and ultrasound have been demonstrated. The spatial resolution of MRI flow velocity measurement is, however, too low, the acquisition time is longer than the cardiac cycle, and the cost is prohibitive. Similarly, the validations performed for this method demonstrate the inability to obtain accurate, time dependent flow velocity profile determination.

Doppler ultrasound mapping of flow velocities is now available for both external and esophageal scanning transducers. Both produce 2D images of intra-ventricular and vascular flow, but the accuracy of the measurements is too low for quantitative evaluation and 3D reconstruction. The application of 2D color flow Doppler techniques to the detection and diagnosis of cardiac and vascular abnormalities is also limited by the inaccurate color flow data provided due to the angular error between the orientation of the Doppler beam and the central axis of the flow field. Intra-vascular probes may produce superior images, but their position within the vessel substantially affects and distorts the 3D pattern of flow. Several groups are concentrating on the development of new probe technology, to acquire flow and structural information, directly in 3D.

There is a need, therefore, for development and improvement of the currently available ultrasound measurement, processing and display techniques for providing accurate Doppler information.

SUMMARY OF THE INVENTION

The present invention provides a method and system for providing corrected Doppler data which is not limited by the disadvantages of the prior art. The invention involves the application of ultrasonic imaging, and particularly Doppler imaging, to provide an accurate representation of blood flow by correcting for the effect of the angle between the flow direction (e.g., the orientation of an imaged artery) and the beam orientation of the ultrasound probe.

A conventional ultrasonic Doppler color mapping system is adapted to include a system to measure and record the free space position and orientation of the ultrasonic probe, as well as a system to generate and record the image acquisition time. Preferably, the position and measurement system is an electromagnetic position/orientation system. Using this system, a set of 2D image planes is acquired, each plane labelled with time, position, and orientation data. Using conventional techniques, an approximation of a 3D structural representation is generated from the acquired data. This 3D reconstruction may be displayed on a monitor which permits a user to define the flow direction (e.g., longitudinal axis of an artery) for the imaged structure or, alternatively, methods may be used to extract the structural information, as well as the flow direction, directly from the 3D reconstruction. Based on this identified flow direction, and the orientation and position information for each acquired 2D slice, the 2D Doppler signals are appropriately transformed into corrected velocity values according to the Doppler look angle. These corrected velocity values may then be used to construct a 3D flow field, preferably represented as a color encoded flow field, which in turn may be superimposed onto the 3D structural representation and displayed according to known methods for representing 3D information. Preferably, the time information is used to provide the corrected Doppler information as a function of time.

BRIEF DESCRIPTION OF THE DRAWINGS

Additional aspects, features, and advantages of the invention will be understood and will become more readily apparent when the invention is considered in the light of the following description made in conjunction with the accompanying drawings, wherein.

DETAILED DESCRIPTION OF A PREFERRED EMBODIMENT

The method and system of the present invention involves the accurate measurement of time-tagged data describing the position and orientation of a 2D Doppler ultrasound probe during the imaging procedure. In this manner, it is possible to generate a set of 2D image planes, labelled with time, position, and orientation data. This provides sufficient information to allow a 3D reconstruction of the imaged structures, as well as the color encoded flow fields. In addition, in accordance with the present invention, the 2D color flow data is processed to provide a corrected color flow map. Uncorrected color flow maps represent velocities in the direction of the ultrasound transducer's axis. The corrected 2D color flow images map the flow velocity field in the direction of the vessel's centerline axis.

Figure 1:
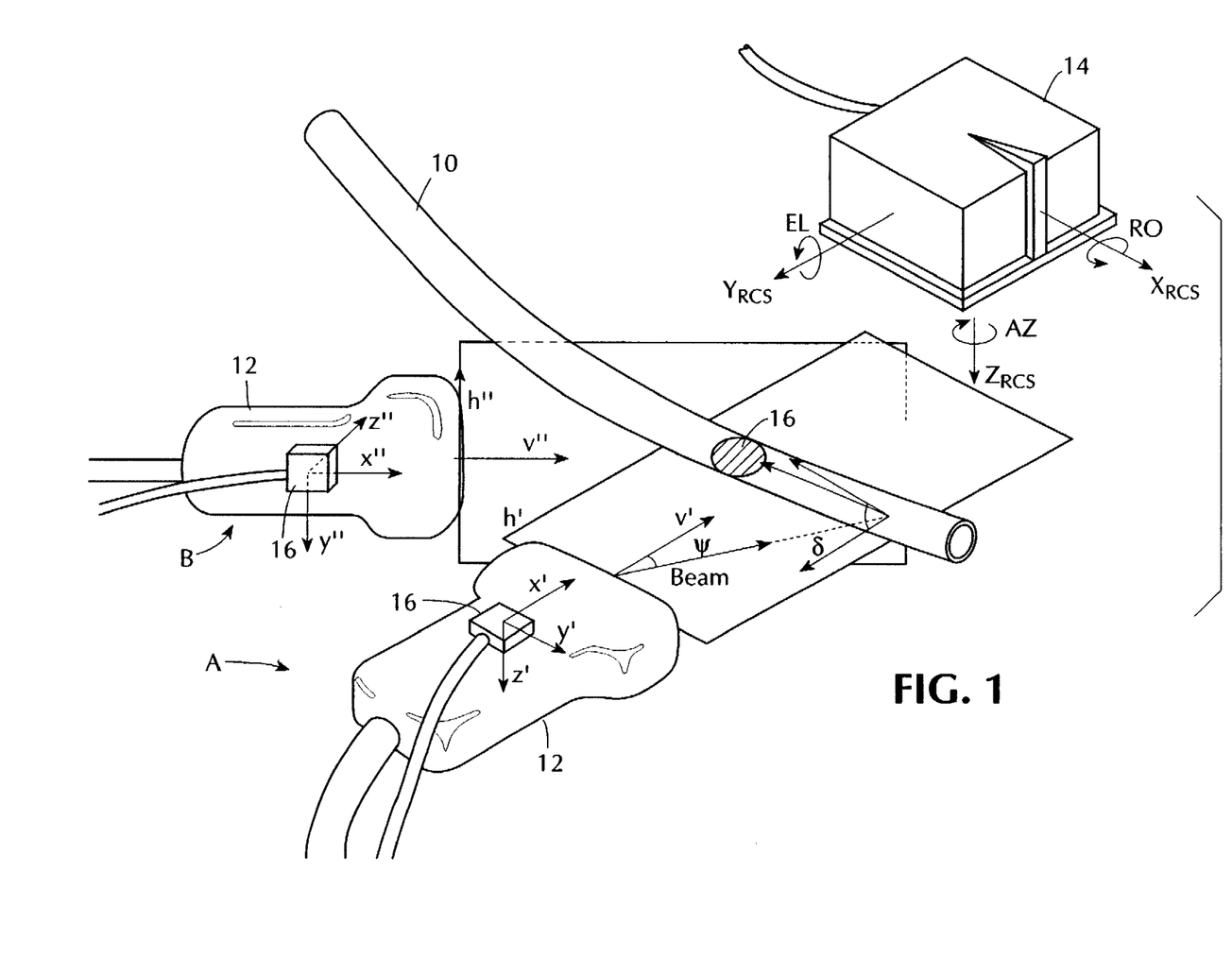
FIG. 1 is a schematic representation of an ultrasound probe oriented transversely and longitudinally with respect to a vessel, and of a position/orientation transmitter and receiver, in accordance with the present invention.

The relationship between the flow direction and the orientation of the ultrasonic probe is illustrated in FIG. 1, which schematically illustrates a vessel 10 and an ultrasonic probe 12, which is shown orientated in two separate positions with respect to the vessel 10. Preferably, the ultrasonic probe 12 is a conventional linear array probe which scans a sector in a plane by steering the direction of the ultrasonic beam according to phase array principles. In a first position A, the ultrasonic probe 12 is shown oriented such that the imaged sector is substantially in the same plane as the longitudinal axis (e.g., flow direction) of the vessel 10, while in position B the ultrasonic probe 12 is shown oriented such that the imaged sector is transverse to the longitudinal axis for the vessel 10. In position B, the intersection of the image plane with the vessel is represented by image slice 16. It may be appreciated that accurately measuring flow velocity via Doppler imaging according to position B requires that the angle between the plane of the image slice 16 (e.g., characterized by vector v") and the flow direction, referred to as the Doppler look angle, should be zero radians. That is, the plane of the image slice 16 should be coincident with the flow direction. It is understood, however, that as a practical matter this condition may not be achieved by a probe that is external to the vessel, and moreover, that according to the prior art the Doppler look angle itself may not be ascertained. The present invention provides for measuring the flow velocity of blood in a vessel, and particularly for measuring the 3D color Doppler image of blood flow in a vessel as a function of time, in accordance with a method and system which corrects the acquired data for the effects of the Doppler look angle, thereby providing accurate velocity flow profiles.

Figure 2:
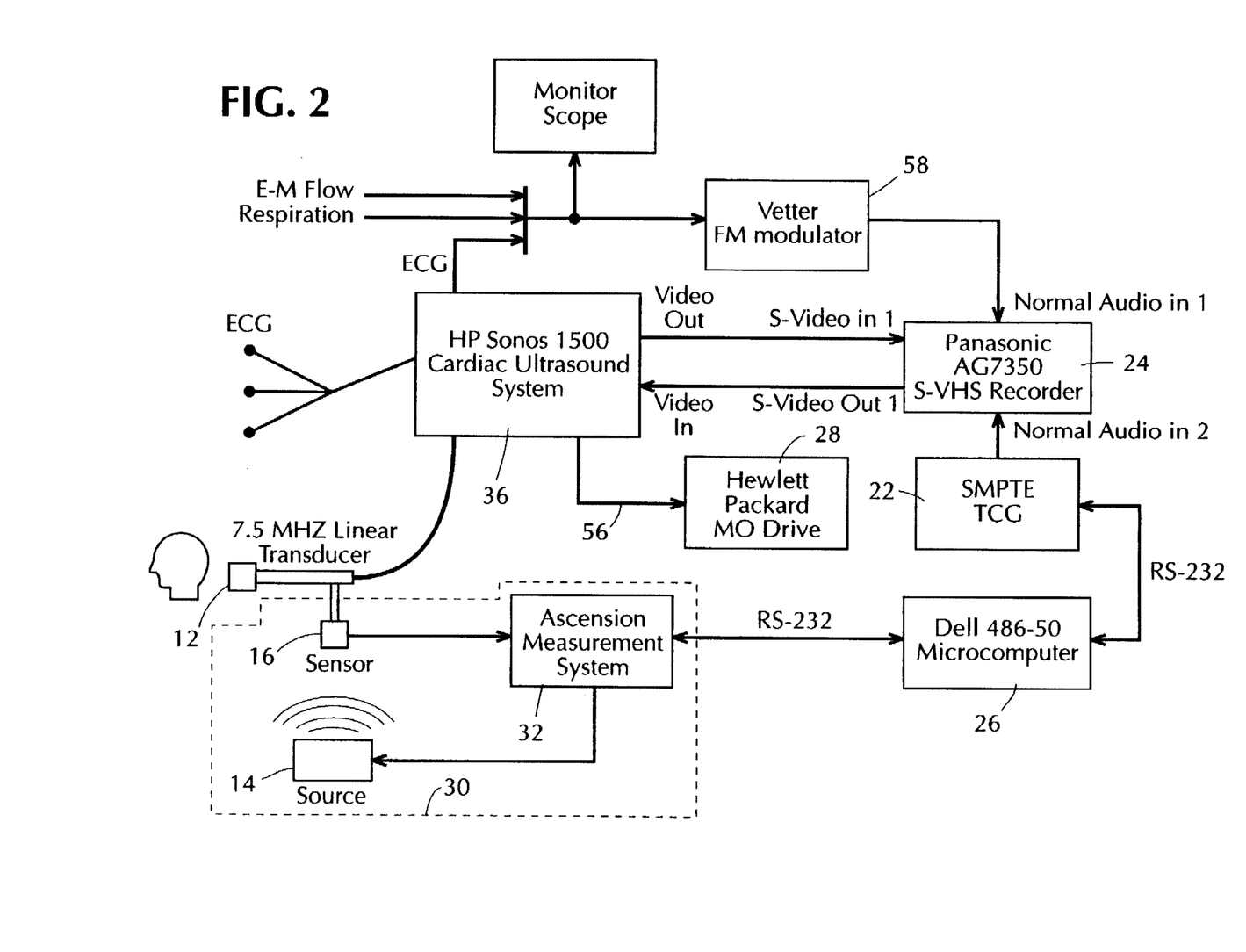
FIG. 2 is a functional block diagram of a system which employs conventional components to provide data acquisition in accordance with the present invention.
Figure 3:
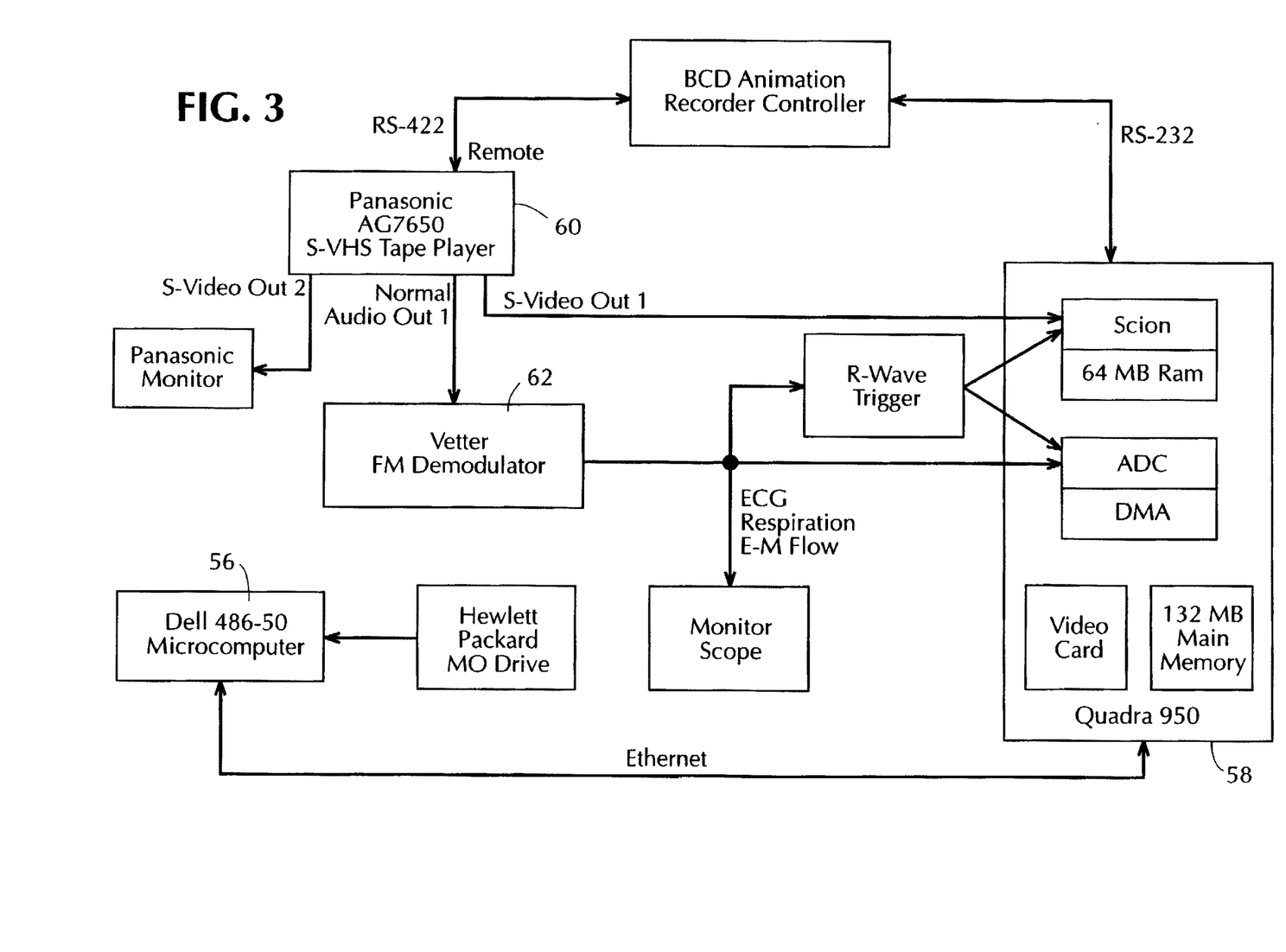
FIG. 3 is a functional block diagram of a system which employs conventional components to provide data processing in accordance with the present invention.

In accordance with the practicing the present invention, FIG. 2 and FIG. 3, by way of example, schematically depict in block diagram form two complementary, microprocessor-based systems that may be employed to accomplish the data collection and analysis tasks. FIG. 2 shows a 3D Doppler Image Acquisition System (3D-DIAS) for use in acquiring the ultrasound information, and FIG. 3 shows a 3D Doppler Image Processing system (3D-DIPS) for use in separate image processing of the acquired data. It is understood that these two systems are shown as a practical way of practicing the present invention based on commercially available components. As may be appreciated by one skilled in the art, and as will be discussed further hereinbelow, the systems shown may be adapted according to other commercially available components as well as according to components that may be designed and constructed by one skilled in the art in light of the present invention to simplify or otherwise optimize the overall system design with respect to practicing the present invention. Preferably, the overall system and method of the present invention may be included into the hardware and software of a commercial ultrasound system to provide corrected color Doppler images as one of the modes available at the bedside in essentially real time.

The 3D-DIAS system shown in FIG. 2 consists of the components necessary to generate and record experiment time, spatial position and orientation of the 2D ultrasound probe 12, and image information. In accordance with a preferred embodiment, the ultrasound probe is operated such that structural image information is acquired in an interleaved manner with respect to Doppler image information (e.g., duplex mode). Time-of-day and frame number data are generated with SMPTE longitudinal time code generator 22 (e.g., Model TRG-50PC, Horita Company, Mission Viejo, Calif., U.S.A.). This device outputs time code continuously as an audio signal on an audio channel of a S-VHS video recorder 24, and via an RS-232 digital data stream to a 486-based, 50 MHz, data logging and control microcomputer 26 (e.g., Model 450DE, Dell Computer Corporation, Austin, Tex., U.S.A.). This microcomputer also collects and logs data from the position/orientation measurement system 30.

Preferably, the position/orientation measurement system 30 is an electromagnetic position/orientation, measurement system (e.g., A Flock of Birds, Ascension Technology Corporation, Buffington, Vt., U.S.A.) which allows the determination of position and spatial orientation of the ultrasound probe 12. This system utilizes a source antenna as a transmitter 14, and a sensor antenna as a receiver 16. The receiver 16 is mounted to the ultrasonic probe 12, while the transmitter 14 is mounted (e.g., on an acrylic shelf) within the vicinity of the spatial region where the ultrasonic probe 12 is used during scanning. Both the transmitter 14 and the receiver 16 contain three orthogonal coils, to generate and detect a quasi-static magnetic field, respectively. With the mentioned commercial position/orientation measurement system, position/orientation determinations can be made at a rate adjustable between 12 and 144 measurements per second. According to an embodiment of the present invention, the report rate within 3D-DIAS system is determined independently, and is equal to video frame rate of the S VHS video recorder 24.

A floating-point processor, within an electronics module 32 of the position/orientation measurement system 30 computes the Position of the receiver 16, in cartesian coordinates, relative to the transmitter 14 (see FIG. 1). In addition, the system computes an Orientation Matrix, which describes the spatial transformation between the respective coordinate systems of the transmitter 14 and receiver 12. This Orientation Matrix is a 3×3 matrix whose elements are functions of the Euler Angles describing the rotations around the axes of the reference coordinate system. An interactive Time, Position and Orientation Measurement System (TPOMS) software environment may be employed on the microcomputer 26 to provide real-time instrument control and data collection. Such a program may be written in Basic (e.g., QuickBasic, V. 4.5, Microsoft Corporation, Redmond, Wash., U.S.A.), and uses the efficient RS-232 Communications, and ASCII character manipulation capabilities provided by the QuickBasic Compiler. Output from TPOMS is a File containing the SMPTE time cede, and transducer position and orientation data for each image frame in a study. By way of example, a study may be composed of multiple 10-second image collection sequences of 301 image frames each.

The images obtained during a study are captured in analog form on S VHS video recorder 24 (e.g., Model AG-7350, Panasonic Corporation, Secaucus, N.J., U.S.A.) and in digital form on a magneto-optical disc drive 28 (e.g., Model 650/A, Hewlett Packard Company, Palo Alto, Calif., U.S.A.). Both of these devices are typically included as components of the Cardiac Doppler Ultrasound System 36 (e.g., Sonos, Model 1500, Hewlett Packard Company, Andover, Mass., U.S.A.), when employed in laboratory studies. It is understood, that in accordance with commercially available components, the Cardiac Doppler Ultrasound System 36 does not provide for storing a time code for each image frame on the magneto-optical disc. One skilled in the art, however, recognizes that it is possible to adapt the Cardiac Ultrasound System 36 to include a time code with each stored image. Further, one skilled in the art recognizes that an alternative way of providing this function is to provide the digital output of the SMPTE longitudinal time code generator 22 and the digital output of the Cardiac Doppler Ultrasound System 36 (i.e., line 56) to a framing instrument (not shown) which combines a time code with each image frame, and outputs this combined digital frame to the magneto-optical disc drive 28. The design of such framing instruments is well known to one skilled in the art of digital design for systems that combine blocks of digital information into an overall frame for further communication. The advantages of including a time code with each frame may be further appreciated in connection with the hereinbelow discussion concerning the correction of the acquired Doppler information.

Preferably, analog waveforms representing the electrocardiogram, respiration, and electromagnetic blood flow (if available), are preferably added to the S-VHS video tape by the use of a 3-channel FM recording adaptor 58 (e.g., Model 3, AR Vetter Co., Rebersburg, Pa., U.S.A.). This device FM modulates three baseband signals into a frequency band compatible with an audio channel of the S-VHS recorder and player 24. This capability permits R-wave gating of the video images for subsequent image averaging, for example, as well as for the elimination of respiratory effects, and for the comparison with direct electromagnetic flow measurement in certain experimental settings. Preferably, the image information stored on the magneto-optical drive 23 includes information that indicates the acquisition time of the image frame with respect to the cardiac and/or respiratory cycle. For instance, in an embodiment in which each frame includes a time code, each frame that occurs at a predetermined time with respect to the cardiac cycle (e.g., coincident with the R-wave trigger) may further be provided with data (e.g., a bit or word) that is indicative thereof. Thus, the time of occurrence for each digitally stored image frame is known with respect to the cardiac cycle (and/or respiratory cycle), thereby facilitating subsequent data analysis.

Referring now to FIG. 3, the 3D-DIPS consists of the components necessary to read and process the 2D color flow images from both S-VHS video tape and magneto-optical disk media. A 486-based, 50 MHz data-formatting and color flow correction microcomputer 56 (e.g., Model 450DE, Dell Computer Corporation, Austin, Tex., U.S.A.) is used for this function. This microcomputer can read the TPOMS Output Files for each study, as well as the magneto-optical disks containing digital color flow images and the structural images. The TPOMS Output Files can, for example, either be transported to 3D-DIPS on floppy disks or sent electronically via Ethernet.

A microcomputer 58, (e.g., Quadra, Model 950, Apple Computer, Inc., Cupertino, Calif., U.S.A.) with 132 MBytes of RAM, contains a high-speed video frame buffer (e.g., Model 2000, Scion Corporation, Frederick, Md., U.S.A.) with 64 MBytes of dedicated image RAM. This platform can directly acquire approximately 7 seconds of 640×480 line video frames, from a S-VHS video player 60 (e.g., Model AG-7650, Panasonic Corporation, Secaucus, N.J., U.S.A.).

The video player 60 can read the SMPTE times codes that are added to an audio channel of the tape during the recording process, as described above in connection with the 3D DIAS. In addition, an FM demodulator 62 is provided for demodulating the waveforms representing the electrocardiogram, respiration, and electromagnetic blood flow (if available) that were modulated onto the audio channel of the videotape. The analog electrocardiogram signal is provided to generate R-Wave triggering for the video frame buffer and for an analog-to-digital converter which digitizes the analog information furnished thereto, and is coupled to a direct memory access means for storage of the digital information that has been converted.

It is understood that the 3D DIPS processes the data stored on the magneto-optical disc which includes separated black-and-white structural images, and color flow images. The S-VHS tape images are actually composite images, with color flow data superimposed on the black-and-white structural data, and therefore they have a number of inherent disadvantages for providing corrected Doppler images. Further it is understood that in accordance with a preferred embodiment of the present invention, since the image data stored on the magneto-optical disc subsystem are R-wave gated at the time of acquisition (by the use of an R-wave trigger internal to the Cardiac Ultrasound System 36), that the digital magneto-optical disc images are preferably processed as a series of data sets, each containing a multiplicity of images that were obtained at the same point in time in the cardiac cycle during successive cardiac cycles.

It is also appreciated that flexible and efficient data collection are possible utilizing the 3D-DIAS described. Similarly, the 3D DIPS also allows an investigator to implement a wide variety of image processing algorithms, from either analog or digital 2D color flow Doppler images.

In accordance with the hereinabove described system, a methodology for practicing the present invention is now further described. The essential steps include acquiring ultrasound structural (e.g., black-and-white or B-mode) and Doppler information, and processing the structural and Doppler information to provide Doppler data that is corrected for the Doppler look angle.

Acquiring such data may occur in a variety of ways. In a dynamic acquisition mode, the ultrasonic probe 12 may be manually scanned over the region of interest while the 3D DIAS acquires information at a predetermined rate and with reference to an internal R-wave trigger. Alternatively, in a static acquisition mode, an operator may manually position the ultrasonic probe 12 in a plurality of fixed positions. At each position, the operator manually initiates the 3D DIAS system to acquire a time series of images for a predetermined period of time over the cardiac cycle. It may also be understood, however, that if the blood flow velocity at only a particular time in the cardiac cycle is desired, in either mode the system may be adapted to acquire data only at the desired point in time, since in both instances the triggering mechanism may be based on the cardiac cycle (e.g., R-wave triggering). During acquisition, a time series of image frames are stored on the magneto-optical drive 28. These image frames are stored as pairs of images, one containing structural information (e.g., black-and-white) and the other containing Doppler information (e.g., color), as discussed above. During acquisition, the time code is provided both to the video recorder 24 and to the microcomputer 26 on a frame by frame basis. For each frame, the microcomputer 26 also acquires the position and orientation information from the position/orientation system 30, and generates and stores the TPOMs file accordingly.

In accordance with an embodiment of the present invention, processing the structural and Doppler information to provide corrected Doppler data is performed using the 3D DIPS such that the structural data is reconstructed to provide flow direction for points along the longitudinal extent of the vessel. This flow direction is used in conjunction with the time coded position and orientation information for the ultrasonic transducer (i.e., TPOMS file) to correct the acquired Doppler data. As discussed above, it is preferable to perform this data analysis for separate points in time with respect to the cardiac cycle since in addition to the dilation and contraction of the vessel diameter during the cardiac cycle, there may also be translational motion of the vessel during the cardiac cycle because of asymmetric mechanical resistance about the vessel. Similarly, flow velocity is apparently a function of time in the cardiac cycle, and the corrected flow velocity should be provided in accordance with the structural reconstruction for substantially the same point in time. It may be appreciated that for practical purposes, image acquisition at a typical video frame rate (e.g., 30 frames per second) is sufficient to consider a subsequent frames of structural and Doppler information as occurring at substantially the same time. As mentioned, for a particular time, a centerline of the vessel is determined according to the structural (e.g. B-mode) data, and the centerline used to compute corrected values for the Doppler data. Thus, corrected Doppler data is provided as a function of time, thereby permitting accurate measurement and visual representation of blood flow as a function of time over the cardiac cycle. It is understood that averaging images which are each identically time locked to the R-wave and each occur in successive cardiac cycles for a plurality of cardiac cycles, either before or after correction, may provide increased signal-to-noise properties.

It may be appreciated that the structural reconstruction may be performed according to structural data obtained simultaneously with the Doppler data (through the use of alternating or time interleaved sequences of structural and Doppler pulses), or in separate measurements over two different series of cardiac cycles. In practice, it has been observed that two measurements of structural data over the cardiac cycle with the ultrasonic probe 12 oriented longitudinally (i.e., position A of FIG. 1) but at different angles about the vessels longitudinal axis is sufficient to provide the structural information needed to extract the flow direction (e.g. centerline axis) along the vessel. Any of myriad 3D reconstruction techniques may be employed to provide a structural representation of the vessel, and further, any of myriad numerical techniques may be employed to select the centerline axis. Also, the centerline essentially may be manually selected by tracing it on a display of the vessel in two planes. It is also understood, that the TPOMs information is also used in the 3D structural reconstruction in order to ensure proper reconstruction as well as spatial correspondence with generated color Doppler images. Moreover, it may be understood, in accordance with discussions hereinabove, that in an embodiment in which the structural and Doppler information stored on the magneto-optical drive does not include R-wave gating information or time code information, that the video information may be used to determine the time position of the image frames stored on the magneto-optic disc by comparison thereof.

In view of the foregoing, it is understood that in accordance with the time code and position/orientation information, the flow direction (e.g., preferably the vessel centerline) for the vessel may be determined. Moreover, this centerline is preferably known as a function of time. The centerline is then used to correct the acquired Doppler information.

Different techniques may attempt to reconstruct and quantify 3D flow profiles similar to the way structures are reconstructed by using temporal and spatial sequential sets of 2D images, and any additional information available. Unfortunately, as discussed above, the Doppler measurement introduces different and additional measurement errors. Unless the image plane coincides with the vascular central longitudinal cross-section the measurement of flow velocity from these images is erroneous. Errors may also be introduced when the flow direction is not taken into account during the calculation of flow velocity. The following techniques are employed to correct the Doppler measurement based on the extracted centerline.

Referring again to FIG. 1, the correction of flow velocity values in images of longitudinal cross-sections (i.e., position A), performed in the image coordinate system ("ICS") is conducted as follows. For each pixel $p_L$ in location $(h_i, v_j)$ within the image, which contains flow velocity values, a correction is made in the ICS, according to the equation:

$$P_{Lcorr}(h_i,v_j) = \frac{P_L(h_i,v_j)}{\cos(\delta)}$$

where $\delta$ is the angle between the flow orientation and the ultrasound probe orientation.

For images acquired with the Linear Array probe, with the beam steered sideways (angle $\Psi$ up to +/−60°), then $$P_{Lcorr}(h_i,v_j) = \frac{P_L(h_i,v_j)}{\cos(\delta - \Psi)}$$

Analogously, correction of flow velocity values in images of transverse cross-sections (i.e., position B), performed in the reference coordinate system ("RCS"), are conducted as follows. For each pixel $P_T$ in location $(h_i, v_j)$ within the image, which contains flow velocity values different than zero flow, a correction is made in the RCS, according to the equation:

$$P_{Lcorr}(h_i,v_j) = \frac{P_L(h_i,v_j)}{\cos \sigma}$$

where $\cos \sigma = D/(magA*magB)$ $D=M_T(1,1)*M_{LR}(1,1)+M_T(2,1)*M_{LR}(2,1)+M_T(3,1)*M_{LR}(3,1)$ $magA=[M_T(1,1)*M_T(1,1)+M_T(2,1)*M_T(2,1)+M_T(3,1)*M_T(3,1)]^{1/2}$ $magB=[M_{LR}(1,1)*M_{LR}(1,1)+M_{LR}(2,1)*M_{LR}(2,1)+M_{LR}(3,1)*M_{LR}(3,1)]^{1/2}$ Matrices $M_L$ and $M_T$ are calculated from the Euler angles of the Ultrasound Probe orientations with respect to the $X_{RCS}, Y_{RCS}, Z_{RCS}$ axes of the Reference Coordinate System as acquired from the position/orientation measurement system 32.

For the longitudinal and transverse cross-sections, respectively, $M_L$ and $M_T$ are defined as:

$$\begin{bmatrix} \cos(y)*\cos(z) & \cos(y)*\sin(z) & -\sin(y) \\ -\cos(x)*\sin(z) & \cos(x)*\cos(z) & \sin(x)*\cos(y) \\ +\sin(x)*\sin(y)*\cos(z) & +\sin(x)*\sin(y)*\sin(z) & \\ \sin(x)*\sin(z) & -\sin(x)*\cos(z) & \cos(x)*\cos(y) \\ +\cos(x)*\sin(y)*\cos(z) & +\cos(x)*\sin(y)*\sin(z) & \end{bmatrix}$$

where matrix $M_{LR}=M_L \times M_R$, and where $M_R$ is Rotational matrix, which transfers the flow orientation from the image plane to the Receiver's coordinate system.

Assuming the flow orientation within the Receiver's x-y image plane, the Euler angles for x, y are both zero, and $z=\delta$, which results in $M_R$ defined as:

$$\begin{vmatrix} \cos(z) & \sin(z) & 0 \\ -\sin(z) & \cos(z) & 0 \\ 0 & 0 & 1 \end{vmatrix}$$

As a result of this methodology, the acquired Doppler information is transformed into corrected Doppler information that may be employed to accurately represent the flow velocity in the vessel as a function of space and time. As evinced by the foregoing description, currently available components may be interconnected to provide a system for practicing this methodology. A preferred implementation of corrected color Doppler imaging in accordance with the present invention should include direct logging of time and position information with the digitally stored image data.

Thus, as illustrated through the preferred embodiment and the foregoing example, and as understood by further practicing the present invention, many advantages and attendant advantages are provided by the present invention. The method developed produces an accurate determination of blood flow velocity non-invasively. This allows not only improved calculation of velocity profiles, flow volume and resistances, but also estimations of pressures across valve orifices and stenotic arteries. The calculation of flow velocity near the arterial walls (currently not computable by most systems), will allow the estimation of shear stress and evaluation of possible future damage to the endothelial surface. Similarly, applying the same procedure to the measurement of the velocity profile across artificial cardiac valves, may provide good estimates of their contribution to blood clot formation. The method provides an important clinical tool for screening and evaluation of vascular pathologies. With further development of Transesophageal Echocardiography, the method may be adapted for evaluating coronary artery stenosis. It may also be appreciated that the present invention provides for free space movement of the ultrasound probe. Thus, the method and system provides for numerous new modalities for medical diagnosis and care.

Although the above description provides many specificities, these enabling details should not be construed as limiting the scope of the invention, and it will be readily understood by those persons skilled in the art that the present invention is susceptible to many modifications, adaptations, and equivalent implementations without departing from this scope. For example, as discussed above, although the invention is described by way of example as including a separate acquisition and processing systems, and an embodiment is disclosed in accordance with convectional, commercially available equipment, one skilled in the art recognizes that the overall invented method and system may be included as a mode of a conventional ultrasound instrument and may be implemented with dedicated hardware and software.

Further, image processing may be simplified by storing all pertinent information digitally within the image frames. Moreover, one recognizes that many image processing and data representation applications and manipulations may be applied to the corrected Doppler data.

These and other changes can be made without departing from the spirit and the scope of the invention and without diminishing its attendant advantages. It is therefore intended that the present invention is not limited to the disclosed embodiments but should be defined in accordance with the claims which follow.

We claim:

1. A Doppler ultrasound apparatus for measuring flow in a localized region within a vessel, said flow having an associated velocity, said apparatus comprising:

an ultrasound probe for generating and detecting an incident and reflected ultrasound signal, respectively, said incident and reflected ultrasound signal including a Doppler ultrasound signal;

a position and orientation system which generates an orientation and position signal for said ultrasound probe; and a processor which provides a corrected ultrasound signal representing said flow, based on said orientation and position signal, and on said ultrasound signal to generate a three-dimensional representation of said vessel for determining a three-dimensional flow direction for said localized region within the vessel;

wherein said corrected ultrasound signal compensates for errors in measuring said flow that are due to angular misalignment of said ultrasound probe relative to said velocity of said flow in said localized region.

2. The apparatus according to claim 1, wherein said ultrasound signal includes Doppler information for a plurality of localized regions within a two dimensional region scanned by said ultrasound probe according to a plurality of scanning lines.

3. The apparatus according to claim 2, wherein said ultrasound probe scans a plurality of two dimensional regions.

4. The apparatus according to claim 3, wherein said plurality of two dimensional regions are scanned as a function of time, and said apparatus provides a time dependent three dimensional flow image.

5. The apparatus according to claim 1, wherein said ultrasound signal includes a structural ultrasound signal.

6. The apparatus according to claim 1, wherein said ultrasound signal includes a time series of structural information and Doppler information.

7. The apparatus according to claim 6, further comprising a means for acquiring said ultrasound signal in a known time relationship with the cardiac cycle of a body observed by the Doppler ultrasound apparatus.

8. The apparatus according to claim 7, wherein said ultrasound signal is acquired over a plurality of cardiac cycles, said processor separately processing data sets of said time series of structural information and Doppler information according to the acquisition time for each data set relative to the cardiac cycle.

9. The apparatus according to claim 7, wherein said corrected ultrasound signal represents a corrected flow velocity.

10. The apparatus according to claim 1, wherein said position and orientation system includes a transmitter and a receiver, one of said transmitter and receiver fixed in space relative to other of said transmitter and receiver, one of said transmitter and receiver fixably mounted to said ultrasound probe, said position and orientation system including a processor for generating an orientation matrix which relates the spatial transformation between the respective coordinate systems of the transmitter and the receiver, thereby providing said orientation and position signal.

11. The apparatus according to claim 1, wherein said processor provides said corrected ultrasound signal based on determining a smooth and continuously changeable central axis for flow according to structural information in said Doppler ultrasound signal.

12. A Doppler ultrasound apparatus for measuring flow velocity in a localized region within a vessel using Doppler ultrasound, said apparatus comprising:

an ultrasound probe for generating and detecting an incident and reflected ultrasound signal, respectively, said incident and reflected ultrasound signal including a Doppler ultrasound signal;

means for generating an orientation and position signal for said ultrasound probe; and means for processing said orientation and position signal, and said ultrasound signal into a corrected ultrasound signal representing said flow velocity based on generating a three-dimensional representation of said vessel for determining a three-dimensional flow direction for said localized region within the vessel;

wherein said corrected ultrasound signal compensates for errors in measuring said flow that are due to angular misalignment of said ultrasound probe relative to said flow velocity in said localized region.

13. The apparatus according to claim 12, further comprising means for generating a time code associated with the time of detecting said ultrasound signal, and wherein said ultrasound signal includes a time series of image data corresponding to a two dimensional region scanned by said ultrasound probe according to a plurality of scan lines.

14. The apparatus according to claim 13, wherein said ultrasound signal includes a image data for a plurality of two dimensional regions, and further comprising means for generating a three dimensional time dependent representation of said flow according to said corrected ultrasound signal.

15. A method for measuring a flow in a localized region within a vessel using a Doppler ultrasound apparatus, said flow having an associated velocity, said method comprising the steps of:

generating and detecting an incident and reflected ultrasound signal, respectively, using an ultrasound probe, said incident and reflected ultrasound signal including a Doppler ultrasound signal;

generating an orientation and position signal for said ultrasound probe; and processing said orientation and position signal, and said ultrasound signal into a corrected ultrasound signal representing said flow by generating a three-dimensional representation of said vessel for determining a three-dimensional flow direction for said localized region within the vessel;

wherein said corrected ultrasound signal compensates for errors in measuring said flow that are due to angular misalignment of said ultrasound probe relative to said velocity of said flow in said localized region.

16. The method according to claim 15, wherein said processing step includes determining a smooth and continuously changeable central axis for flow according to structural information in said Doppler ultrasound signal.

17. The method according to claim 15, further comprising the step of generating a three dimensional flow image according to said corrected ultrasound signal.

18. The method according to claim 17, wherein said three dimensional flow image corresponds to flow at a particular time with respect to the cardiac cycle of a body observed by the Doppler ultrasound apparatus.

19. The method according to claim 17, further comprising the step of generating said three dimensional flow image as a function of time.

20. The apparatus according to claim 1, wherein said ultrasound signal includes a structural ultrasound signal in addition to the Doppler ultrasound signal, and wherein said processor provides said corrected ultrasound signal based on determining a smooth and continuously changeable central axis for flow according to the structural ultrasound signal.

* * * * *